United States Patent [19]
Beitzke et al.

[11] Patent Number: 5,399,773
[45] Date of Patent: Mar. 21, 1995

[54] PROCESS FOR THE PREPARATION OF NITROPHENYL ALKYL ETHERS

[75] Inventors: Bernhard Beitzke, Rösrath; Robert Weitz, Bergisch Gladbach, both of Germany

[73] Assignee: Bayer Aktiengesellschaft, Leverkusen, Germany

[21] Appl. No.: 893,615

[22] Filed: Jun. 5, 1992

[30] Foreign Application Priority Data

Jun. 14, 1991 [DE] Germany .................. 41 19 664.3

[51] Int. Cl.$^6$ ........................................... C07C 201/12
[52] U.S. Cl. ..................................... 568/30; 568/36; 568/44; 568/586; 568/587; 568/630; 568/939
[58] Field of Search ................... 568/586, 587, 30, 44, 568/36, 630, 939

[56] References Cited

U.S. PATENT DOCUMENTS 2,312,801  3/1943  Craig et al. .................. 568/586 X
4,377,712  3/1983  Foster et al. .................. 568/586 X

FOREIGN PATENT DOCUMENTS 1532235  4/1968  France .

OTHER PUBLICATIONS

World Patents Index Latest Week, No. 8442, 1984.
World Patents Index Latest Week, No. 9041, 1990.
Beilstein, 4th Ed, vol. VI, p. 412 (1923).
Beilstein, 4th Ed., vol. VI EI p. 206, (1923).
Houben–Weyl, 4th Ed., vol. VI/3 (1965), p. 54ff.
Fierz–David, Grundlegende Operationen der Farbenchemie, 8th Ed., (1952), p. 143.

*Primary Examiner*—Johann Richter
*Assistant Examiner*—Michael B. Hydorn
*Attorney, Agent, or Firm*—William C. Gerstenzang

[57] ABSTRACT

Nitrophenyl alkyl ethers can be advantageously prepared by reacting a nitrophenol with an alkyl halide in water as the reaction medium in such a manner that the nitrophenol is laid before with the water and the alkyl halide and a hydrogen halide-binding compound are then added simultaneously.

19 Claims, No Drawings

PROCESS FOR THE PREPARATION OF NITROPHENYL ALKYL ETHERS

BACKGROUND OF THE INVENTION

1. Field of the Invention

The invention relates to a process for the preparation of nitrophenyl alkyl ethers from nitrophenols and alkyl halides in the presence of hydrogen halide-binding compounds, which is characterised in that water is used as the reaction medium, and also in that nitrophenol is laid before with the water and the alkyl halide and the hydrogen halide-binding compound are then added simultaneously, Nitrophenyl alkyl ethers are important organic intermediates, for example in the preparation of dyes.

2. Description of the Related Art

Beilstein, 4th edition, Volume VI, p. 412 (1923), discloses the preparation of 2-nitro-4-methyl-phenyl methyl ether from dry 2-nitro-p-cresol in the form of the silver salt and methyl iodide diluted with ether.

Houben-Weyl, 4th edition, Volume VI/3 (1965), p. 54ff., discloses the alkylation of phenolates with alkyl halides in an aqueous medium. However, as soon as the phenolates bear a nitro group, this reaction is carried out in an organic solvent, such as cyclopentanone or xylene (loc. cit., p. 56). Fierz-David, Grundlegende Operationen der Farbenchemie (Fundamental operations in colour chemistry), 8th edition (1952), p. 143, also mentions methanol or ethanol as the reaction medium.

In addition, the use of another alkylation agent, that is dimethyl sulphate in conjunction with potassium carbonate using xylene as solvent, is known (Beilstein, 4th edition, Volume VI EI, p. 206).

Various disadvantages are associated with the processes of the prior art. Thus the introduction of all of the nitrophenol in the form of the phenolate is a safety risk, and, moreover, leads to problems on stirring and to a poor conversion rate owing to the poor solubility of the nitrophenolate. If all of the reactants are introduced together and completely, there is the danger of a spontaneous reaction in which the exothermic heat of reaction can no longer be removed rapidly enough. With the use of alcohols as reaction medium there is furthermore the danger of unwanted ether formation with the alkyl halide reactant.

SUMMARY OF THE INVENTION

A process has been found for the preparation of nitrophenyl alkyl ethers of the formula

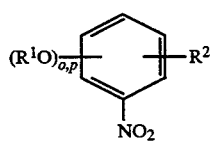

(I)

in which
$R^1$ is straight-chain or branched $C_1$-$C_4$-alkyl,
o,p indicates the ortho- or para-position of $R^1O$ to the nitro group and
$R^2$ represents hydrogen, straight-chain or branched $C_1$-$C_8$-alkyl, $C_3$-$C_8$-cycloalkyl, $C_7$-$C_{10}$-aralkyl, $C_6$-$C_{12}$-aryl, aryl, straight-chain or branched $C_1$-$C_8$-alkoxy, straight-chain or branched $C_1$-$C_8$-alkylthio, $C_6$-$C_{12}$-aryloxy, $C_6$-$C_{12}$-arylthio, —SO$_2$—$R^3$, —SO$_2$—OR$^3$, —SO$_2$—NR$^3{}_2$, —SOR$^3$, fluorine, chlorine or bromine, in which
$R^3$ represents $C_1$-$C_4$-alkyl,
by reacting the base nitrophenols with alkyl halides in the presence of hydrogen halide-binding compounds, which is characterised in that a nitrophenol of the formula

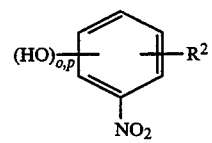

(II)

in which
o,p indicates the ortho- or para-position of the hydroxyl group to the nitro group and
$R^2$ has the meaning given above,
is reacted with 100–200 mol %, relative to the amount of the nitrophenol, of an alkyl halide of the formula
$$R^1\text{—}X \quad \text{(III)},$$
in which
$R^1$ has the meaning given above and
X represents chlorine or bromine,
in the presence of 80–130 equivalent %, relative to the amount of the alkyl halide, of a hydrogen halide-binding compound selected from the group comprising the hydroxides, carbonates and hydrogen carbonates of the alkali(ne earth) metals in such a manner that the nitrophenol is introduced into the water used as reaction medium, where the quantity of water must at least be sufficient to dissolve all resulting inorganic salts, and the alkyl halide and the hydrogen halide-binding compound are added simultaneously, and where the reaction is carried out in the temperature range from 20° to 200° C. and in the pressure range from 1 to 50 bar, and in the absence or presence of a bromide or iodide of an alkali(ne earth) metal in an amount of 0 to 10 mol %, relative to the nitrophenol to be reacted.

DETAILED DESCRIPTION OF THE INVENTION

Straight-chain or branched $C_1$-$C_8$-alkyl is, for example, methyl, ethyl, propyl, isopropyl, butyl, isobutyl or the isomeric hexyls or octyls. A preferred alkyl has 1 to 4 C atoms, and is particularly preferably methyl or ethyl, and very particularly preferably methyl.

$C_3$-$C_8$-cycloalkyl is, for example, cyclopropyl, cyclobutyl, cyclopentyl, cyclohexyl, cycloheptyl or cyclooctyl, preferably cyclopropyl, cyclopentyl or cyclohexyl.

$C_7$-$C_{10}$-aralkyl is, for example, benzyl, phenylethyl or phenylpropyl, preferably benzyl.

$C_6$-$C_{12}$-aryl is, for example, phenyl, naphthyl or biphenylyl, preferably phenyl.

The alkyl and/or aryl moieties in the further meanings for $R^2$, that is alkoxy, alkylthio, aryloxy or arylthio are composed analogously to those described above.

Nitrophenols of the type described for use in the process according to the invention and methods for their preparation are known to those skilled in the art.

In a preferred manner, a nitrophenol of the formula

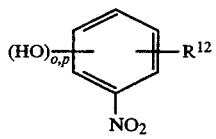

is used, in which
- o,p indicates that the ortho- or para-position of the hydroxyl group to the nitro group and
- $R^{12}$ is hydrogen, straight-chain or branched $C_1$–$C_4$-alkyl, benzyl, phenyl, straight-chain or branched $C_1$–$C_4$-alkoxy or phenoxy.

In a particularly preferred manner, a nitrophenol of the formula

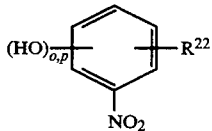

is used, in which
- o,p has the meaning given above and
- $R^{22}$ is hydrogen or straight-chain or branched $C_1$–$C_4$-alkyl.

In a very particularly preferred manner, a nitrophenol of the formula

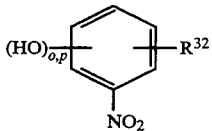

is used, in which
- o,p has the meaning given above and
- $R^{32}$ represents hydrogen or methyl.

In the above formulae for the nitrophenols to be used according to the invention, the letters "o,p" indicate the ortho- or the para-position of the hydroxyl group to the nitro group, so that according to the invention ortho-nitrophenol or para-nitrophenol or their derivatives substituted by $R^2$, $R^{12}$, $R^{22}$ or $R^{32}$ are used.

In a preferred manner, however, the ortho-nitrophenols are used.

In a preferred manner, therefore, according to the invention an ortho-nitrophenol of the formula

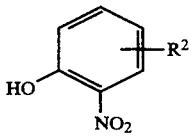

is used, in which
- $R^2$ has the range of meanings given above.

In a particularly preferred manner an ortho-nitrophenol of the formula

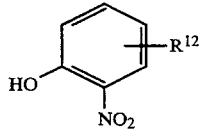

is used, in which
- $R^{12}$ has the range of meanings given above.

In a very particularly preferred manner an ortho-nitrophenol of the formula

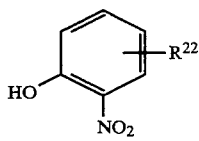

is used, in which
- $R^{22}$ has the meaning given above.

The process according to the invention for the use of an ortho-nitrophenol of the formula

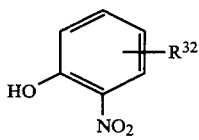

in which
- $R^{32}$ is hydrogen or methyl is of particularly great importance.

The reaction according to the invention is carried out with an alkyl halide of the formula (III). Examples of such alkyl halides are methyl chloride, methyl bromide, ethyl chloride, ethyl bromide, propyl chloride, propyl bromide, isopropyl chloride, isopropyl bromide, 1-butyl chloride, 1-butyl bromide, 2-butyl chloride, 2-butyl bromide, isobutyl chloride and isobutyl bromide.

In a preferred manner, the reaction is carried out using an alkyl halide of the formula $$R^{11}\text{—}X \qquad (XI)$$

in which
- $R^{11}$ is methyl or ethyl and
- X represents chlorine or bromine.

In a further preferred manner, methyl chloride or methyl bromide is used as the alkyl halide; the use of methyl chloride is very particularly preferred.

The hydrogen halide-binding compounds that can be used are the hydroxides, carbonates and hydrogen carbonates of alkali(ne earth) metals known to those skilled in the art. In a preferred manner, the hydrogen halide-binding compounds are hydroxides and/or carbonates of sodium and/or potassium. In a particularly preferred manner, a mixture of sodium hydroxide and potassium hydroxide in a molar ratio of 5:1 to 1:5 is used. A variant of particular processing importance on account of the good metering ability is the use of such a mixture of sodium hydroxide and potassium hydroxide in the form of a 10 to 60% strength by weight aqueous solution.

The reaction medium in the process according to the invention is water. Organic solvents, such as those used in the prior art cited, are therefore avoided completely.

The quantity of water is selected so that all the resulting inorganic salts are dissolved. This quantity of water is at least 150 g per mole of nitrophenol to be reacted, and covers the range 150 to 1000 g, preferably 150 to 500 g per mole of nitrophenol.

The process according to the invention can be carried out in the absence or presence of a bromide or iodide of an alkali(ne earth) metal. Where such a salt is present, a bromide or iodide of an alkali metal is preferably selected. Such salts are only required in catalytic quantities, covering the range 0 to 10 mol %, preferably 0 to 5 mol %, particularly preferably 0.1 to 2 mol %, relative to the nitrophenol to be reacted. The lower limit of zero indicates that in many cases such a catalytic addition can be avoided completely.

Such avoidance is possible, for example, with the use of potassium hydroxide as the hydrogen halide-binding compound; in the case of compounds of other cations, the bromides and iodides mentioned are advantageously used to accelerate the reaction.

It is, moreover, astonishing, in a multi-phase reaction of this type, that phase transfer catalysts, such as for example quaternary ammonium salts or crown ethers, can be avoided completely.

The process according to the invention is carried out in the pressure range from 1 to 50 bar, preferably 2 to 30 bar, particularly preferably 2 to 15 bar, and in the temperature range from 20° to 200° C., preferably 50 to 150° C., particularly preferably 80° to 130° C.

A further characteristic of the process according to the invention is that the nitrophenol is introduced into the water used as the reaction medium, and the alkyl halide and the hydrogen halide-binding substance are added simultaneously. The abovementioned total amount of water comprises the water introduced simultaneously with the nitrophenol and the water required for dissolution of the hydrogen halide-binding compound. However, it is possible in principle to meter in the hydrogen halide-binding compound as a solid simultaneously with the alkyl halide, the total amount of water in such a case being introduced simultaneously with the nitrophenol.

The quantity of alkyl halide and the hydrogen halide-binding compound to be added simultaneously is generally at least 100 mol % or 100 equivalent %, respectively, of the nitrophenol to be reacted. If smaller quantities of alkyl halide and hydrogen halide-binding compound are used, the reaction according to the invention is possible in principle, but cannot by nature give a high yield. To achieve as high a yield as possible, on the other hand, the alkyl halide and the hydrogen halide-binding compound to be metered in simultaneously thereto are preferably used in excess. The quantities used are therefore in the range from 100 to 200 mol %, preferably 120 to 160 mol %, for the alkyl halide, relative to the nitrophenol to be reacted, and in the range from 80 to 130 equivalent %, preferably 100 to 110 equivalent % for the hydrogen halide-binding compound, relative to the alkyl halide used.

For the preferred case when excess alkyl halide is used, it is furthermore advantageous, after addition of roughly the stoichiometric amount of the alkyl halide (about 100 mol %), to add the amount in excess of this at a reduced rate. During the addition of the excess alkyl halide, it is possible to depart from the simultaneous addition of the hydrogen halide-binding compound, in so far as the completion of the addition of the hydrogen halide-binding compound occurs later than the completion of the addition of the excess alkyl halide.

The process according to the invention is carried out in a suitable stirred vessel, for example an autoclave equipped with a stirrer. After completion of the reaction of the process according to the invention, the reaction mixture is worked up so that the organic and the aqueous phase are separated, the aqueous phase is subsequently extracted with a suitable solvent such as xylene, toluene, etc., the previously separated organic phase is combined with the extract, and these combined organic phases, after washing with water, are worked up by conventional methods, such as distillation or crystallisation, to obtain the desired nitrophenyl alkyl ethers.

The process according to the invention is distinguished by a number of advantages from processes of the prior art. Thus, the simultaneous metering of alkylation agent and hydrogen halide-binding compound gives increased safety, since the steady state concentration of nitrophenolate is kept very low. Nitrophenolates are known to have a tendency to strong exothermic decomposition. The process according to the invention avoids the introduction of nitrophenolate as an additional solid phase, thus making the alkylation easier and avoiding encrustations on the reactor walls. The use of water as the sole reaction medium has a number of safety advantages compared with the hitherto used flammable organic solvents. The use of water as the reaction medium has an additional advantage, in that the wash water produced during workup of one reaction batch can be returned to the reaction of a later batch. Furthermore, the formation of ethers, which occur with the use of alcohols as solvents, is prevented, thus facilitating the purification of the waste air. The avoidance of phase transfer catalysts according to the invention avoids the otherwise inevitable effluent contamination. Furthermore, preliminary conversion of the nitrophenol to be reacted into the phenolate in a separate process step is not required.

Example 1 o-Nitro-p-cresol was reacted with methyl chloride in a 71 autoclave. The autoclave was equipped with a stirrer and metering equipment, and also for measurement of temperature and pressure.

1610 g (10.52 mol) of o-nitro-p-cresol were introduced in 2630 g of water. The mixture was subsequently heated to 110° C., an autogenous pressure of 1.5 bar being produced.

In 4 hours, 991 g of a 50% strength alkali metal hydroxide solution (molar ratio NaOH:KOH=7:3) and 532 g of chloromethane were simultaneously metered in with stirring, during which the pressure rose to 8 bar. Subsequently, 566 g of alkali metal hydroxide solution were metered in 4 hours, and, beginning at the same time, but ending after 2 hours, 319 g of chloromethane were metered in during which the pressure rose to 10 bar. After half an hour of further reaction, the mixture was cooled to room temperature, the pressure was released from the autoclave and the reaction mixture was removed. A further 660 g of water were used during this for rinsing.

For the work-up, the autoclave contents together with the rinsing water were heated to a sump temperature of 105° C. to remove all volatile components. After cooling to 55° C., the mixture was left to stand to separate the organic and the aqueous phases. The organic phase was washed with water, which can be used in a following reaction batch. The aqueous phase was extracted with xylene. The washed organic phase and the xylene extract were again washed with water and then distilled on a rotary evaporator to remove the remaining water. After complete removal of xylene by distillation, 1712 g of 2-nitro-4-methylmethoxybenzene were obtained in a purity of 98.4%; this corresponds to 1683.8 g of a 100% pure product, and thus to 95.8% of the theoretical yield.

EXAMPLE 2

The procedure of Example 1 was followed, but in the first 4 hours 758 g of 50% strength NaOH were metered in, and, in the second phase, 708 g of 50% strength KOH. After work-up, 2-nitro-4-methyl-methoxybenzene was obtained in a yield of 94.8% of theory.

EXAMPLE 3

The procedure of Example 1 was followed, but in the first 4 hours 842 g of 50% strength NaOH were metered in, and, in the second phase, 421 g of 50% strength NaOH and 266 g of chloromethane.

After work-up, 2-nitro-4-methyl-methoxybenzene was obtained in a yield of 92.3% of theory.

EXAMPLE 4

The procedure of Example 1 was followed, but only 2200 ml of water were introduced.
Yield: 91.8% of theory.

EXAMPLE 5

The procedure of Example 1 was followed, but 30 g of sodium iodide were introduced together with the water. In the first 4 hours 842 g of 50% strength NaOH were metered in, and in the second phase in 4 hours 505 g of 50% strength NaOH were metered in, and in 2 hours—beginning at the same time—319 g of chloromethane.
Yield after work-up: 96.3% of theory.

EXAMPLE 6

The procedure of Example 1 was followed, but 1610 g (10.52 mol) of 4-nitro-3-methyl-phenol were used. After work-up, 1652 g of 4-nitro-3-methyl-anisole were isolated in a purity of 99%; this corresponds to a yield of 93% of theory. Freezing point 46° C.

EXAMPLE 7

The procedure of Example 1 was followed, but 1465 g (10.52 mol) of o-nitrophenol were introduced in 2630 g of water at 50° C.

In 4 hours, 991 g of a 50% strength alkali metal hydroxide solution (molar ratio NaOH:KOH=7:3) and 676 g of ethyl chloride were simultaneously metered in with stirring, the autoclave being held at the pressure produced internally.

Subsequently, 472 g of alkali metal hydroxide solution were added in 4 hours, and, beginning at the same time, 340 g of ethyl chloride were metered in 2 hours. After work-up, 1688 g of o-nitrophenetol were obtained in a purity of 99%; that corresponds to a yield of 95% of theory. Boiling point 144° C./10 mbar.

What is claimed is:

1. A process for the preparation of a nitrophenyl alkyl ether of the formula

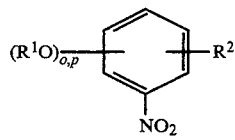

in which
R$^1$ is straight-chain or branched C$_1$–C$_4$-alkyl,
o,p indicates the ortho- or para-position of R$^1$O to the nitro group and
R$^2$ is hydrogen, straight-chain or branched C$_1$–C$_8$-alkyl, C$_3$–C$_8$-cycloalkyl, C$_7$–C$_{10}$-aralkyl, C$_6$–C$_{12}$-aryl, straight-chain or branched C$_1$–C$_8$-alkoxy, straight-chain or branched C$_1$–C$_8$-alkylthio, C$_6$–C$_{12}$-aryloxy, C$_6$–C$_{12}$-arylthio, —SO$_2$—R$^3$, —SO$_2$—OR$^3$, —SO$_2$—NR$^3{}_2$, —SOR$^3$, fluorine chlorine or bromine, in which
R$^3$ is C$_1$–C$_4$-alkyl,
consisting essentially of reacting a nitrophenol of the formula

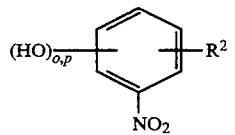

in which
o,p indicates the ortho- or para-position of the hydroxyl group to the nitro group and
R$^2$ has the meaning given above,
with 100–200 mol %, relative to the amount of the nitrophenol, of an alkyl halide of the formula

R$^1$-X in which
R$^1$ has the meaning given above and
 is chlorine,
in the presence of 80–130 equivalent %, relative to the amount of the alkyl halide, of a hydrogen halide-binding compound selected from the group consisting of the hydroxides, carbonates and hydrogen carbonates of the alkali and alkaline earth metals in such a manner that the nitrophenol is introduced into water which is used as the reaction medium, and wherein the quantity of said water used as a reaction medium is at least sufficient to dissolve all resulting inorganic salts, and wherein the alkyl halide and the hydrogen halide-binding compound are added simultaneously, the reaction is carried out in the temperature range from 20° to 200° C., a pressure range from 1 to 50 bar, and in the absence or presence of a bromide or iodide of an alkali or alkaline earth metal in an amount of 0 to 10 mol % relative to the nitrophenol to be reacted.

2. The process of claim 1, wherein the nitrophenol is reacted with 120–160 mol % of the alkyl halide.

3. The process of claim 1, wherein the reaction is carried out in the presence of 100–110 equivalent % of the hydrogen halide-binding compound.

4. The process of claim 1, wherein a nitrophenol of the formula

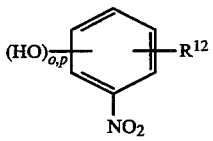

in which
- o,p indicates the ortho- or pare-position of the hydroxyl group to the nitro group and
- $R^{12}$ is hydrogen, straight-chain or branched $C_1-C_4$-alkyl, benzyl, phenyl, straight-chain or branched $C_1-C_4$-alkoxy or phenoxy, is used.

5. The process of claim 4, wherein a nitrophenol of the formula

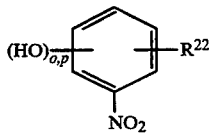

in which
- o,p has the meaning given above and
- $R^{22}$ is hydrogen or straight-chain or branched $C_1-C_4$-alkyl, is used.

6. The process of claim 5, wherein a nitrophenol of the formula

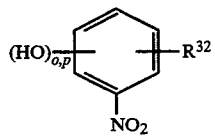

in which
- o,p has the meaning given above and
- $R^{32}$ is hydrogen or methyl, is used.

7. The process of claim 1, wherein an ortho-nitrophenol of the formula

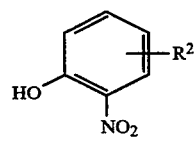

in which
- $R^2$ is hydrogen, straight-chain or branched $C_1-C_8$-alkyl, $C_3-C_8$-cycloalkyl, $C_7-C_{10}$-aralkyl, $C_6-C_{12}$-aryl, straight-chain or branched $C_1-C_8$-alkoxy, straight-chain or branched $C_1-C_8$-alkyl-thio, $C_6-C_{12}$-aryloxy, $C_6-C_{12}$-arylthio, $-SO_2-R^3$, $-SO_2-OR^3$, $-SO_2-NR^3{}_2$, $-SOR^3$, fluorine, chlorine or bromine, in which
- $R^3$ is $C_1-C_4$-alkyl, is used.

8. The process of claim 7, wherein an ortho-nitrophenol of the formula

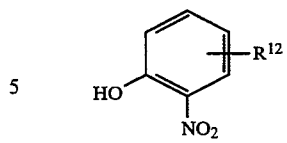

in which
- $R^{12}$ is hydrogen, straight-chain or branched $C_1-C_4$-alkyl, benzyl, phenyl, straight-chain or branched $C_1-C_4$-alkoxy or phenoxy, is used.

9. The process of claim 8, wherein an ortho-nitrophenol of the formula

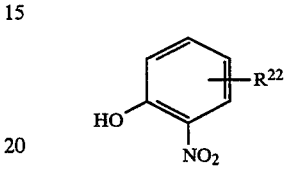

in which
- $R^{22}$ is hydrogen or straight-chain or branched $C_1-C_4$-alkyl, is used.

10. The process of claim 9, wherein an ortho-nitrophenol of the formula

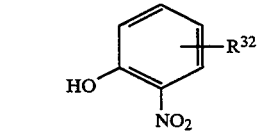

in which
- $R^{32}$ is hydrogen or methyl, is used.

11. The process of claim 1, wherein an alkyl halide of the formula $$R^1-X$$

in which
- $R^1$ is methyl or ethyl and
- X represents chlorine, is used.

12. The process of claim 11, wherein methyl chloride is used.

13. The process of claim 1, wherein the hydrogen halide-binding compound used is a hydroxide or a carbonate of sodium or potassium or a mixture thereof.

14. The process of claim 13, wherein a mixture of NaOH and KOH in a molar ratio of 5:1 to 1:5 is used.

15. The process of claim 1, wherein the quantity of water in the reaction mixture is 150 to 1000 g per mole of nitrophenol to be reacted.

16. The Process of claim 1, which is carried out in the absence or presence of a bromide or iodide of an alkali metal in a quantity of 0 to 5 mol %, relative to the nitrophenol to be reacted.

17. The process of claim 1, which is carried out in the pressure range from 2 to 30 bar.

18. The process of claim 1, which is carried out in the temperature range from 50° to 150° C.

19. The process of claim 1, wherein when an excess amount of the alkyl halide, relative to nitrophenol, is used, the amount of alkyl halide in excess of the stoichiometric amount is added at a reduced rate, and the completion of the addition of the hydrogen halide-binding compound occurs later than the completion of the addition of the alkyl halide.

* * * * *

UNITED STATES PATENT AND TRADEMARK OFFICE
CERTIFICATE OF CORRECTION

PATENT NO. : 5,399,773

DATED : March 21, 1995

INVENTOR(S) : Beitzke, et al.

It is certified that error appears in the above-identified patent and that said Letters Patent is hereby corrected as shown below:

| | |
|---|---|
| Title Page | ABSTRACT: Line 4 delete " laid before with the water " and substitute -- introduced into the water which is used as the reaction medium -- |
| Col. 4, lines 46 & 49 | Delete " $R^{11}$ " and substitute -- $R^1$ -- |
| Col. 8, line 44 | Before " is " insert -- X -- |

Signed and Sealed this

Twenty-seventh Day of June, 1995

Attest:

BRUCE LEHMAN

Attesting Officer

Commissioner of Patents and Trademarks